(12) United States Patent
Pratt

(10) Patent No.: US 6,167,962 B1
(45) Date of Patent: Jan. 2, 2001

(54) ANTI-WOBBLING BAILER WITH HIGH SPEED INSERTION

(76) Inventor: David W. Pratt, 13512 Feather Sound Cir. West, Clearwater, FL (US) 33760

(*) Notice: Under 35 U.S.C. 154(b), the term of this patent shall be extended for 0 days.

(21) Appl. No.: 09/349,068

(22) Filed: Jul. 8, 1999

(51) Int. Cl.[7] .............................. E21B 31/08; G01N 1/12
(52) U.S. Cl. ..................... 166/162; 73/864.63; 166/99
(58) Field of Search ........................... 166/66, 162, 165, 166/66.6, 66.7, 99; 73/864.02, 864.31, 864.63

(56) References Cited

U.S. PATENT DOCUMENTS

| | | | | |
|---|---|---|---|---|
| 2,454,740 | * | 11/1948 | Lehnhard, Jr. | 166/66 |
| 2,856,005 | * | 10/1958 | Beck | 166/162 |
| 2,951,538 | * | 9/1960 | Martin | 166/162 |
| 4,590,810 | * | 5/1986 | Hunkin et al. | 73/864.63 |
| 5,454,275 | * | 10/1995 | Kabis | 73/864.51 |
| 5,597,966 | * | 1/1997 | Timm | 73/864.63 |
| 5,878,813 | * | 3/1999 | Ridgeway, Jr. | 166/162 |

* cited by examiner

Primary Examiner—Frank Tsay
(74) Attorney, Agent, or Firm—Ronald E. Smith; Smith & Hopen, P.A.

(57) ABSTRACT

A bailer has two externally-mounted weights. The first weight is positioned at the uppermost end and the second weight is positioned at the lowermost end of the bailer. The combination of weights increases the insertion rate of the bailer into a liquid so that the time elapsed for an insertion is reduced relative to the time required to insert unweighted bailers, top-weighted bailers, or bottom-weighted bailers. The weights also prevent wobble about the longitudinal axis of the bailer as it descends. The external mounting of the weights further prevents contamination of the liquid collected by the bailer and eliminates back pressure and turbulence caused by interior weights.

3 Claims, 1 Drawing Sheet

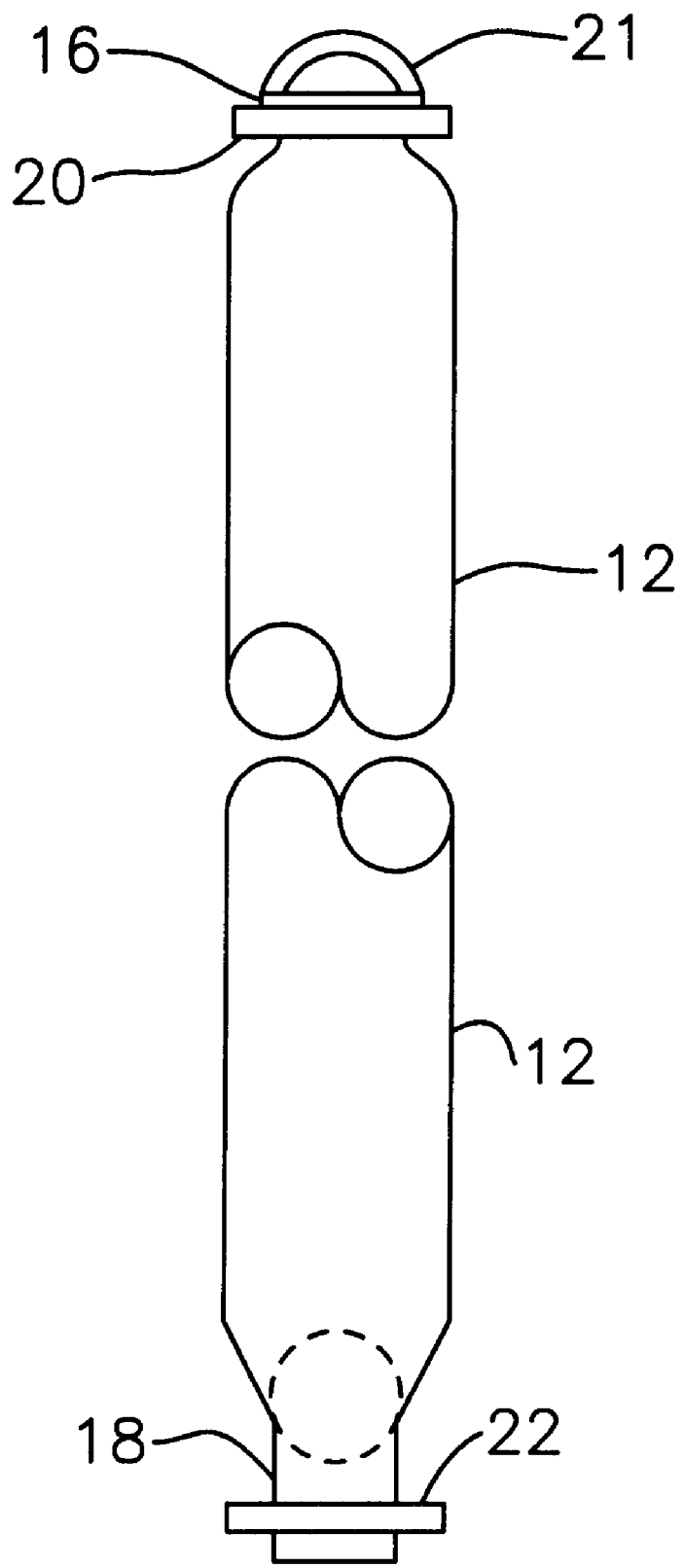

ANTI-WOBBLING BAILER WITH HIGH SPEED INSERTION

BACKGROUND OF THE INVENTION

1. Field of the Invention

This invention relates, generally, to bailers. More particularly, it relates to a bailer having enhanced utility in applications where liquid samples are taken at substantial distances below the surface of the earth.

2. Description of the Prior Art

Bailers are hollow, cylindrical devices of elongate construction used to take samples of liquids from various locations such as wells, tanker trucks, barrels and the like. A bailer has a one-way valve at its lowermost end that admits a liquid into the hollow interior of the bailer when the bailer is lowered and that closes when the bailer is lifted so that the collected liquid does not leak out.

There are two shortcomings with the bailers heretofore known that relate to deep well applications. Deep wells typically include a plurality of twenty foot long pipes arranged end-to-end with one another, in a vertical stack. It is virtually impossible to align each pipe in precise concentric alignment with its contiguous pipe when the pipes are driven into the earth. As a result, a ridge is formed every twenty feet where two pipes meet in a slightly eccentric relation to one another.

A conventional bailer lowered down into a deep well will wobble about its longitudinal axis as it descends. Its lowermost or leading end will encounter these ridges when the wobble is at its maximum and get caught, unable to descend further until the rope or whatever device is used to lower it is jiggled or otherwise manipulated to cause the bailer to dislodge from a ridge and continue its descent. If it drops only another twenty feet and encounters another ridge, the freeing process must be repeated again. Obviously, where a bailer is being lowered hundreds or even thousands of feet, a considerable amount of time can be spent in dislodging it from the ridges it encounters during its descent.

A bailer that could be lowered great distances without becoming lodged on such ridges would have increased value over conventional bailers. It would save significant amounts of time and effort.

Unweighted bailers take a half minute or more to fully enter the liquid being sampled. This time adds up when many samples are taken.

There is a need, therefore, for a bailer that becomes fully immersed within a liquid in a shorter time than conventional bailers.

Some bailers heretofore known are equipped with a weight means to increase their rate of insertion into a liquid. However, the weight means is positioned within the hollow interior of the bailer where it may contaminate the sample and where it constricts the free flow of liquid into the hollow interior of the bailer. Such constriction increases the time required for the submersion of the bailer.

Some bailer manufacturers position a weight means at the lowermost end of the bailer, and some position a weight means at the uppermost end of the bailer. Significantly, although a top-mounted or a bottom-mounted weight means will decrease the insertion time of a bailer, it will not prevent the bailer from wobbling about its longitudinal axis during its descent and becoming lodged against the abovementioned projecting ridges.

There is one bailer that is manufactured to have a rounded leading end to overcome the lodging problem, but it still has a relatively poor rate of insertion.

If a bailer could be designed that would enter into a sample liquid quickly, and not become lodged on pipe ridges as it is lowered into a deep well, and not collect sediment created by impact, it would greatly increase the productivity of the bailer industry.

However, it was not obvious to those of ordinary skill in this art how such a bailer could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention. The bailer of this invention includes an elongate main body having a hollow interior. The elongate main body has an uppermost end and a lowermost end and a one-way valve means is positioned within the hollow interior near the lowermost end to admit liquid into the hollow interior when the bailer is lowered into a liquid. The one-way valve also prevents leakage of the liquid from the hollow interior when the bailer is lifted from the liquid.

A first weight means is secured to the uppermost end of the main body and a second weight means is secured to the lowermost end of the main body.

Accordingly, the bailer enters into a liquid at an insertion rate that is faster than insertion rates for bailers lacking top and bottom weight means. Moreover, the bailer has minimal wobble about its longitudinal axis when it is lowered so that it does not become lodged against ridges formed by misaligned pipes.

The top and bottom weight means are mounted externally of the hollow interior so that liquid collected within the hollow interior is not contaminated by the weight means and so that the weight means does not form an obstacle to the free flow of liquid into the hollow interior.

It is a primary object of this invention to provide a bailer that drops into a deep well without becoming hung up or otherwise lodged against projections formed by eccentrically aligned pipe sections.

Another object is to provide a bailer that inserts itself quickly into a liquid, thereby shortening the time required to perform a sampling.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a side elevational view of the novel bailer.

DETAILED DESCRIPTION OF THE PREFERRED EMBODIMENT

Referring now to FIG. 1, it will there be seen that an exemplary embodiment of the invention is denoted as a whole by the reference numeral 10.

Bailer 10 has a hollow cylindrical main body 12. Ball valve 14, which forms no part of this invention, is positioned within the hollow interior of main body 12 at its lowermost or leading end and acts as a one-way valve to admit liquid into the hollow interior as the bailer is lowered into liquid. The valve closes to prevent leakage when the bailer is lifted from a liquid.

In the preferred embodiment of the novel bailer, the uppermost or trailing end 16 thereof has a diameter less than that of main body 12, as does the lowermost or leading end 18.

A first weight means 20 is secured by suitable means to uppermost end 16 of bailer 10 and a second weight means 22 is secured by suitable means to lowermost end 18. Both weight means are positioned externally of the hollow interior of the bailer for two reasons. First of all, such external mounting ensures that the liquid being collected cannot be contaminated by contact with the weights. Secondly, the externally mounted weights do not constrict the free flow of liquid into the hollow interior of the bailer. This eliminates the back pressure presented to the liquid by internally-mounted weights. It further eliminates the turbulence caused by internally-mounted weights.

Handle 21 that surmounts bailer 10 is conventional. A rope is tied to it to facilitate lowering bailer 10 into a well.

Bailer 10 inserts itself into a liquid far faster than an unweighted bailer. Moreover, the presence of two weight means at the respective leading and trailing ends of the bailer prevents wobble of the bailer about its longitudinal axis as it descends down a well. Therefore, its leading end does not contact the sidewalls of the pipes and does not encounter ridges formed by eccentrically-aligned pipes.

Weights 20, 22 may be equal in weight to one another or they may differ in weight.

Insertion and wobble tests were performed using bailers manufactured by different companies. The speed of insertion of the bailer into the liquid being sampled was measured by a digital stop watch. Three measurements were taken for each insertion and the three measurements were averaged to arrive at an insertion time, measured to within a tenth of a second. Unweighted bailers as well as bailers having externally mounted and internally mounted weights were tested, as were all combinations of top-mounted, bottom-mounted, and top and bottom-mounted weights, it being understood that only the bailer of this invention includes a top and bottom weight means.

The following bar chart graphically depicts the results of the experiments that were conducted. The vertical axis indicates seconds. The number under each bar indicates the relative amount of wobble of the bailer being tested, where the number one represents little or no wobble, the number two represents a significant amount of wobble, and the number three indicates an excessive amount of wobble. Thus, a bailer with a wobble rating of two would become lodged on some ridges as it descended and a bailer with a wobble rating of three would become lodged on almost every ridge as it descended. A bailer with a wobble rating of one would seldom or never contact a ridge during its descent.

All bailers were forty two inches in length. The "heavy" weights were five ounces and the "light" weights were four ounces. The liquid was clear fresh water.

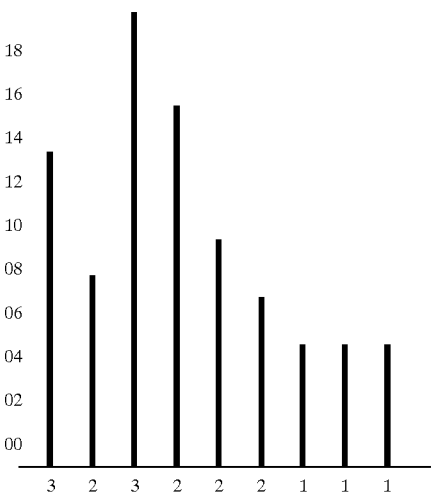

Reading the bar chart from left to right, the first bailer was bottom-weighted with a light weight and took about 13 seconds to insert itself into the liquid. The wobble rating was three.

The second bailer was top-weighted with a light weight and took about seven and a half seconds to insert itself. It had a wobble rating of two.

The third bailer was unweighted and took much longer than twenty seconds to insert itself and therefore its bar would not fit onto the chart; it had a wobble rating of three.

The fourth bailer, like the first, was bottom-weighted with a light weight and had an insertion time of slightly over fifteen seconds and a wobble rating of two.

Bailer number five was bottom-weighted with a heavy weight and had an insertion rate of slightly less than nine seconds. It had a wobble rating of two.

The sixth bailer was top-weighted with a heavy weight and had an insertion rate of slightly over six seconds. It had a wobble rating of two.

Bailers numbered seven, eight and nine were top and bottom-weighted with external weights all had an insertion rate of about four seconds and a wobble rating of one. The top and bottom weights of bailer number seven were equal to one another. Bailer number eight had a light top weight and a heavy bottom weight. Bailer number nine had a heavy top weight and a light bottom weight.

Only the top and bottom-weighted bailers had an acceptable wobble rating and were thus immune to becoming stuck when descending through pipe sections of imperfect alignment. Moreover, they had the shortest insertion time.

All bailers descend in liquid at the same rate after full immersion because all weights sink at the same rate. Thus, the seventh, eighth and ninth bailers sink when fully immersed at the same rate as the other seven bailers. It follows that the decreased insertion rate is not just the obvious result of adding a second weight means to a weighted bailer because adding a second weight means would have no effect on the sinking rate of an immersed bailer.

The reduced insertion rate therefore appears to be a function of the uppermost weight being acted upon by gravity while it is still in the air. The uppermost weight drives the lowermost weight to sink initially at a faster rate than it would under its own power.

The reduced wobble rate appears to be a function of the mounting of the respective weight means at the top and bottom ends of the novel bailer. Bailers having top weights or bottom weights alone have unacceptable wobble ratings.

This invention represents a major breakthrough in the art of bailers. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A bailer, comprising:

an elongate main body having a hollow interior;

said elongate main body having an uppermost end and a lowermost end;

a one-way valve means positioned within said hollow interior near said lowermost end thereof to admit liquid into said hollow interior when said bailer is lowered into a liquid and to prevent leakage of said liquid from said hollow interior when said bailer is lifted from said liquid;

a first weight means secured to said uppermost end of said main body; and a second weight means secured to said lowermost end of said main body;

said top and bottom weight means being mounted externally of said hollow interior;

whereby liquid collected within said hollow interior is not contaminated by said weight means;

whereby said weight means does not form an obstacle to the free flow of liquid into said hollow interior;

whereby said bailer is inserted into a liquid at an insertion rate that is faster than insertion rates for bailers lacking said top and bottom weight means; and whereby said bailer has minimal wobble about its longitudinal axis when it is lowered so that it does not become lodged against ridges formed by misaligned pipes.

2. The bailer of claim 1, wherein said first and second weight means have a common weight.

3. The bailer of claim 1, wherein said first and second weight means have weights that are different from one another.

* * * * *